United States Patent [19]
Small et al.

[11] Patent Number: 4,904,484
[45] Date of Patent: Feb. 27, 1990

[54] PROCESS FOR TREATING COFFEE BEANS WITH ENZYME-CONTAINING SOLUTION UNDER PRESSURE TO REDUCE BITTERNESS

[75] Inventors: Leonard E. Small; Thomas N. Asquith, both of Cincinnati, Ohio

[73] Assignee: The Procter & Gamble Company, Cincinnati, Ohio

[21] Appl. No.: 179,703

[22] Filed: Apr. 11, 1988

[51] Int. Cl.$^4$ .......................... A23F 5/04; A23F 5/10; A23F 5/14

[52] U.S. Cl. ........................................ 426/45; 426/63; 426/595; 426/61

[58] Field of Search ...................... 426/45, 44, 63, 594, 426/595, 7, 61

[56] References Cited

U.S. PATENT DOCUMENTS

| | | | |
|---|---|---|---|
| 2,278,473 | 0/1941 | Musher | 426/595 |
| 3,106,470 | 10/1963 | Spotholz | 426/447 |
| 3,399,998 | 12/1968 | Morrison | 426/445 |
| 3,589,911 | 6/1971 | Friedman | 99/68 |
| 3,644,122 | 2/1972 | Yeransian | 426/459 |
| 3,705,810 | 12/1972 | Lendvay | 426/45 |
| 3,845,220 | 10/1974 | Suzuki | 426/45 |
| 3,983,002 | 9/1976 | Ohya et al. | 435/822 |

FOREIGN PATENT DOCUMENTS

| | | | |
|---|---|---|---|
| 226095 | 6/1987 | European Pat. Off. | |
| 49-12710 | 3/1974 | Japan | 426/45 |

*Primary Examiner*—Marianne Cintins
*Attorney, Agent, or Firm*—Eric W. Guttag; Chester Cekala; Richard C. Witte

[57] ABSTRACT

A process for treating green or partially roasted coffee beans to improve flavor and reduce bitterness in the resulting roast and ground coffee product is disclosed. The green or partially roasted beans are treated with a solution containing cell-wall-digesting, cell-storage-component-digesting or phenol oxidase enzymes under a pressure of at least about 250 psi. The treated beans are then dried, roasted to their final roast color and ground in a conventional manner to provide roast and ground coffee products having "Toddy"-like aroma and flavor. Sugars and foodgrade bases can also be included in the enzyme-containing solution to enhance the level of desirable coffee aroma and flavor components.

11 Claims, No Drawings

PROCESS FOR TREATING COFFEE BEANS WITH ENZYME-CONTAINING SOLUTION UNDER PRESSURE TO REDUCE BITTERNESS

TECHNICAL FIELD

This application relates to a process for treating green or partially roasted coffee beans to improve flavor and reduce bitterness in the resulting roast and ground coffee products. This application further relates to a preferred process for enhancing the level of desirable flavor and aroma components in such coffee products.

Coffee products referred to as "Toddy" coffee have been found to have preferred aroma and flavor characteristics relative to conventionally prepared roast and ground coffee products. "Toddy" coffee has been described as mild and aromatic with a sweet, caramel-like taste. The preferred aroma and flavor character of "Toddy" coffee is based on relatively high levels of certain desirable coffee aroma and flavor components. These desirable flavor components include aldehydes, diketones, pyrazines, and caramel compounds such as furaneol.

The preferred aroma and flavor character of "Toddy" coffee is also due to a much lower level of certain undesirable coffee flavor components. These undesirable flavor components include the guaiacols, as well as other phenolic compounds. Guaiacols contribute a bitter, burnt, smoky-type flavor impression to the coffee. Compared to "Toddy" coffee products, conventionally prepared roast and ground coffee products have a more bitter and burnt flavor character due to a significantly higher level of the guaiacols.

"Toddy"-like flavor can be obtained by removing these guaiacols (plus other bitter phenolic compounds) from the coffee beans prior to final roasting. For example, green coffee beans can be partially roasted to further develop greater quantities of guaiacols and their respective precursors. The guaiacols and their precursors are then removed by soaking the partially roasted beans in water, typically for a period of from 8 to 16 hours. After soaking for this period of time, the guaiacol-enriched solution is drained off, followed by conventional roasting (and grinding) of the dried, guaiacol-depleted coffee beans. Unfortunately, the time required to soak these partially roasted coffee beans is too long to be practical for preparing commercial quantities of roast and ground coffee products and can cause undesirable fermentation of the beans.

This soaking method can be improved by speeding up the removal rate of guaiacols and other bitter phenolic compounds from the coffee beans. One such improvement involves soaking the partially roasted coffee beans in a guaiacol-depleted coffee liquor solution to remove the guaiacols (and guaiacol precursors) from the partially roasted coffee beans. (This guaiacol-depleted liquor can be obtained by soaking other partially roasted beans in water and then treating the resulting coffee liquor to remove the guaiacols and respective precursors.)

While treatment of the partially roasted beans with the guaiacol-depleted coffee liquor speeds up the process of guaiacol removal, it is still fairly slow, typically requiring 4 to 8 hours when carried out under ambient conditions. Moreover, at the same time that the guaiacols are removed, the liquor solution can also remove desirable coffee aroma and flavor components from the partially roasted beans. Accordingly, it would be desirable to develop a process for treating these partially roasted beans which would more quickly remove the guaiacols and other bitter phenolic compounds without causing other undesirable effects, in particular the removal of desirable aroma and flavor components.

In addition to removing guaiacols, it would be beneficial to enhance the level of desirable aroma and flavor components in "Toddy" coffee products. For example, coffee beans can be impregnated with solutions containing precursors and generators of these desirable coffee aroma and flavor components. Accordingly, a process which simultaneously removes guaiacols while at the same time impregnating the beans with desirable aroma/flavor precursors and generators would be extremely useful.

BACKGROUND ART

U.S. Pat. No. 2,278,473 to Musher, issued Apr. 7, 1941, discloses a process for subjecting green or roasted coffee to pressures of from about 20 to about 450 psi, at temperatures of from about 250° to about 700° F. (from about 121° to about 371° C.) for a period of time ranging from about 5 seconds to about 10 minutes. The pressure is then instantaneously released to make the coffee more porous for subsequent treatment or impregnation with air, moisture, steam, various solvents or various flavoring materials. The porous nature of the treated bean is also said toe enable heat to enter more quickly and uniformly during subsequent roasting.

U.S. Pat. No. 3,983,002 to Ohya et al, issued Sept. 28, 1976, discloses that hemicellulase (a cell-wall digesting enzyme), when incorporated into roast coffee beans, increases their extractability.

U.S. Pat. No. 3,644,122 to Yeransian, issued Feb. 22, 1972, discloses the treatment of ground roasted coffee with alkaline materials, e.g. ammonia, prior to extraction to provide a darker colored coffee product having increased yield of soluble solids.

DISCLOSURE OF THE INVENTION

The present invention relates to a process for treating coffee beans to reduce the bitterness of the resulting roast and ground coffee products. This process comprises the steps of:

(1) providing coffee beans selected from green coffee beans, and partially roasted green coffee beans; and (2) treating the coffee beans with a treatment solution containing an effective amount of an enzyme selected from cell-wall-digesting enzymes, cell-storage-component-digesting enzymes, phenol oxidase enzymes and mixtures thereof for a period of from about 1 to about 90 minutes at a temperature of from about 20° to about 100° C. and under a pressure of at least about 250 psi.

The treated beans can then be dried (if needed), roasted to their final roast color and ground in a conventional manner to provide roast and ground coffee products having "Toddy"-like aroma and flavor characteristics.

The process of the present invention has a number of advantages in providing roast and ground coffee products having "Toddy"-like aroma and flavor characteristics. In particular, the process of the present invention greatly reduces the treatment time required to remove guaiacols and other bitter-tasting phenolic compounds. In addition to preventing fermentation of the beans, this reduced treatment time means that less of the desirable coffee aroma/flavor components are removed. Also, the resulting roast and ground coffee products have increased flavor strength. In addition to removing guaiacols, the process of the present invention can be used to enhance the level of desirable coffee aroma and flavor components when the treatment solution additionally, and preferably, contains sugars and foodgrade bases in appropriate amounts.

A. Partial Roasting of Green Coffee Beans

The process of the present invention generally works with any starting blend of undecaffeinated or decaffeinated green coffee beans. The three major types of coffee beans are the milds, the Brazilians, and the Robustas. Botanically, the milds and the Brazilians are traditionally thought of as the Arabicas. The milds give coffee brew which are more fragrant and acidic. Brazilian beans result in coffee brews which are relatively neutral flavored. The Robusta beans produce brews with strong distinctive flavors that possess varying degrees of rubbery notes. Traditionally, the milds are the most expensive of the three types of beans, with the Brazilians being of intermediate expense, and the Robustas being the least expensive. Most roast and ground coffee products involve a blend of these three varieties of coffee beans.

In using the process of the present invention, better results can usually be obtained with a starting blend of coffee beans which comprise a greater quantity of high quality coffee. For example, preferably less than about 50% of the green coffee beans are of the lower quality Robusta type, while more than about 50% of the beans are of the higher quality Arabicas. Since the process of the present invention retains the good aroma and flavor components of the starting beans, a naturally better roast and ground coffee product can be obtained when the starting beans contain a greater quantity of higher quality green coffee beans. Even though better results can be obtained with blends containing greater quantities of higher quality beans, the process of the present invention still provides improvements for any blend of green coffee beans.

In the process of the present invention, the green coffee beans can be used as is, or are preferably partially roasted, usually to a Hunter L-color of from about 26 to about 60. Preferably, the coffee beans are partially roasted to a Hunter L-color from about 26 to about 44, and most preferably to from about 26 to about 39. As used herein, the Hunter Color "L" scale system defines the color of the coffee beans and the degree to which they have been roasted. A complete technical description of the system can be found in an article by R. S. Hunter, "Photoelectric Color Difference Meter," *J. of the Optical Soc., of Amer.*, Vol. 48, pp. 985-95 (1958), which is incorporated by reference. Hunter Color "L" scale values are units of light reflectance measurement. The higher the value, the lighter is the color since a lighter colored material reflects more light. In the Hunter Color system the "L" scale contains 100 equal units of division; absolute black is at the bottom of the scale ($L=0$) and absolute white is at the top ($L=100$). Accordingly, in measuring degrees of roast, the lower the "L" scale value, the greater is the degree of roast, i.e., the darker is the color of the roasted bean.

The green coffee beans can be partially roasted using any suitable roasting process which can achieve the above roast colors. Typically, partial roasting is conducted at a temperature of from about 230° to about 370° C. for from about 2 to about 6 minutes, at atmospheric pressure. After partial roasting, the coffee beans are preferably dried, typically to a moisture content from about 1.5 to about 7%, and preferably to moisture content of from about 1.5 to about 4%. As an alternative to drying, the beans can be less quenched with water at the end of the partial roasting step to achieve this lower moisture level. Drying or less quenching increases the ability of the partially roasted beans to absorb the treatment solution.

The partial roasting step is preferred for the process of the present invention because it develops more fully the components responsible for bitter taste, in particular the guaiacols, which are then removed by the treatment step described hereafter. Partial roasting, and the subsequent treatment step, also alter the precursors and generators responsible for coffee aroma and flavors in a manner that enhances the development of desirable aromas and flavors. In addition, it has been found that partial roasting of the coffee beans makes them more porous and thus improves the ability to impregnate them with solutions containing coffee aroma/flavor precursors and generators, e.g. sugars and foodgrade bases. Accordingly, the partial roasting and treatment steps successfully interfere with the roasting reactions in a manner that favorably modifies the chemistry of the resulting roast and ground coffee product. In general, the roast and ground coffee products obtained according to the present invention taste less bitter and have more or better aroma and flavor.

B. Treatment of Green or Partially Roasted Beans

1. Treatment Solution

The treatment solution used in the process of the present invention contains, as its active component, certain enzymes; optionally, but preferably, sugars and foodgrade bases; if desired, other optional aroma and flavor precursors/generators. This solution can formed by simply combining these active components with water (i.e., an aqueous solution), with a foodgrade organic solvent such as ethyl acetate, ethanol or coffee oil (i.e., an organic solution), or with a mixed solvent system (e.g., water and ethyl acetate). Treatment solutions can also be formulated by combining these active components with extracts or liquors obtained from coffee bean sources. Suitable sources of coffee extract or coffee liquor can be obtained from green coffee beans, partially roasted green coffee beans, or completely roasted (and ground) coffee beans. Extracts or liquors obtained from coffee bean sources are preferred from the standpoint of minimizing the removal of desirable coffee aroma and flavor components. In this regard, coffee liquors or extracts obtained from partially roasted beans are considered to be particularly preferred.

Extracts can be obtained from completely roasted and ground coffee beans by any suitable method for obtaining coffee extracts used in preparing soluble or "instant" coffee products. In the case of green or partially roasted coffee beans, the beans are typically ground and then soaked in ambient temperature water (e.g. about 22° C.) for a certain period of time, e.g. at least about 16 hours for partially roasted beans, at least about 24 hours for green coffee beans. The resulting liquor is then separated from the ground beans. The extracts or liquors obtained typically contain from about 1 to about 35% coffee solids, and preferably from about 3 to about 20% coffee solids. These levels of coffee are sufficient to reduce the loss of desirable coffee aroma and flavor components during the treatment step according to the process of the present invention.

The liquors or extracts obtained from coffee sources can be used as is. However, these coffee liquors or extracts are preferably treated to at least partially deplete them, and preferably essentially deplete them, of guaiacols, as well as other biter phenolic compounds. One method for depleting the coffee liquor or extract of guaiacols is by contact with a suitable resin which has an affinity for phenolic compounds, and especially guaiacols. Suitable resins for this purpose include beta-cyclodextrin polymers, Amberlite nonionic polymeric adsorbent resins, such as XAD-4, XAD-7, XAD-8 and XAD-16, sold by Rohm & Haas, or other nonionic polymeric adsorbent resin. Another method for depleting the coffee liquor or extract of guaiacols is to contact it with an appropriate phenol oxidase enzyme (e.g., catechol oxidase, laccase, cresolase, monophenol oxidase or diphenol oxidase). Suitable sources of phenol oxidase enzymes include tyrosinase, phenolase, as well as plant extracts such as tea extracts, apple juice, pear juice and grape juice containing phenol oxidase enzymes. Coffee liquors obtained from partially roasted green beans which have been depleted of guaiacols by resin treatment have been found to be particularly suitable as treatment solutions in the process of the present invention.

A particularly important component of the treatment solution is the enzyme which is selected from cell-wall-digesting enzymes, cell-storage-component-digesting enzymes, phenol oxidase enzymes, as well as mixtures of these enzymes. As used herein, the term "cell-wall-digesting enzymes" refers to an enzyme which is capable of breaking down one or more coffee cell wall constituents to simpler materials and thus reduces the structural integrity or increases the permeability of the cell wall. Coffee cell walls are composed primarily of cellulose and hemicellulose, but contain lesser amounts of glucans, mannans, pectins and lignins. Accordingly, suitable cell-wall-digesting enzymes include cellulases and hemicellulases (e.g. rohalase, rohapect and rohament, made by Rohmtech), pectinases, glucanases, mannases, and ligninases.

As used herein, the term "cell-storage-component-digesting enzymes" refers to an enzyme which is capable of breaking down components stored in the coffee cell. These stored components typically generate coffee aroma and flavor precursors. Suitable cell-storage-component-digesting enzymes include the amylases, glucosidases, mannosidases, dextranases, proteases such as papain and coralase L10, exoproteases, endoproteases, phosphatases, phytases, phospholipases, lipases and nucleases.

As used herein, the term "phenol oxidase" refers to an enzyme which is capable of oxidizing, or otherwise chemically altering the phenolic compounds (or their precursors) present in coffee beans before or after development by roasting. The guaiacols, which are the important bitter phenolic compounds, can be chemically altered fairly readily by phenol oxidase enzymes. The phenol oxidase enzymes include the catechol oxidases, laccases, cresolases, monophenol oxidases and diphenol oxidases. Examples of suitable phenol oxidase enzymes include tyrosinase, phenolase, as well as plant extracts such as tea extracts, apple juice, pear juice and grape juice containing phenol oxidase enzymes. Particularly preferred enzymes for inclusion in the treatment solution are tyrosinase (a phenol oxidase), phenolase (a phenol oxidase), rohalase (a hemicellulase), and coralase L10 (a protease), sold by Rohmtech.

These enzymes are included in the treatment solution in an effective amount. What constitutes "an effective amount" will depend on the particular enzyme involved, the effects desired during treatment of the green or partially roasted beans, the particular treatment conditions used, and like factors. Typically, the enzyme is included in the treatment solution in an amount of from about 0.0005 to about 0.1% by weight of the beans. Preferably, the enzyme is included in the treatment solution in an amount of from about 0.005 to about 0.05% by weight.

In addition to the enzymes, the treatment solution can optionally and preferably contain aroma and flavor precursors and generators which enhance the level of desirable coffee aroma and flavor components in the resulting roast and ground coffee product. A preferred precursor/generator which can be included in the treatment solution is sugar. As used herein, the term "sugar" refers to the mono- and di-saccharides based on hexoses such as maltose, glucose and fructose, and pentoses such as ribose, arabinose and xylose. Examples of suitable sugars include sucrose, fructose, glucose, high fructose corn syrup, invert sugar, high maltose corn syrups and the like, as well as mixtures of these sugars. Particularly preferred sugars for the purposes of the present invention are sucrose, fructose, glucose, and mixtures thereof.

The amount of sugar included in the treatment solution can vary depending on the particular sugar or sugar mixture used, the flavor enhancement effects desired, the treatment conditions used and like factors. Typically, the sugars are included in the treatment solution in an amount of from about 2.5 to about 50% by weight of the solution. Preferably, the treatment solution comprises from about 5 to about 20% by weight sugar.

In addition to the sugars, another preferred aroma/flavor precursor and generator included in the treatment solution is a foodgrade base. Suitable foodgrade bases include sodium hydroxide, ammonium hydroxide, potassium hydroxide, calcium hydroxide, sodium carbonate, ammonium carbonate, potassium carbonate, calcium carbonate, sodium bicarbonate, ammonium bicarbonate, potassium bicarbonate, and mixtures thereof. Ammonium hydroxide is a particularly preferred foodgrade base for inclusion in the treatment solution.

Like the sugars, the foodgrade base can be included in varying amounts depending on the type of base involved, the flavor enhancement effects desired, the treatment conditions used and like factors. Typically, the foodgrade base is included in the treatment solution in an mount of from about 0.005 to about 0.02% by weight of the solution. Preferably, the foodgrade base is included in an mount of from about 0.01 to about 0.02% by weight. An important factor in determining how much base is included is the pH of the resulting treatment solution. This pH needs to be monitored to control the decomposition of sugars present in the treatment solution. In this regard, formulating the treatment solution to have a pH of from about 4.0 to about 7.5 is preferred for the purpose of controlling the decomposition of sugars to enhance aroma.

In addition to sugars and foodgrade bases, other optional aroma/flavor precursors can be included in the treatment solution. These optional precursors include amino acids, organic phosphates (e.g., phospholipids such as lecithin), polysaccharides such as maltodextrins, and commercially available coffee flavor compounds and compositions such as cyclotene, maltol, 5-hydroxymaltol, furaneol, vanillin and mixtures thereof.

The weight ratio of the treatment solution to the green or partially roasted beans can be varied depending on the particular composition of the treatment solution, the particular flavor effects desired and the particular treatment conditions used. Usually, this weight ratio of solution to beans is adjusted to maximize the removal rate of guaiacols and other bitter phenolic compounds, while at the same time minimizing the removal of desirable coffee aroma and flavor components. Usually, the weight ration of treatment solution to beans is from about 1:10 to about 5:1. Preferably, this weight ratio is from about 1:6 to about 3:1, and most preferably from about 1:2 to about 2:1.

2. Treatment Conditions

The particular conditions under which the green or partially roasted beans are treated with the solution of enzymes, and optionally, but preferably sugars, food-grade bases and other flavor precursors/generators, has been found to be particularly important to the process of the present invention. The key treatment conditions include: (1) the duration of treatment; (2) the temperature at which the treatment is carried out; and (3) in particular, the pressure under which treatment is carried out. These three key process conditions can be varied in order to maximize the desirable benefits of the process of the present invention. These benefits include maximizing the removal of guaiacols and other bitter phenolic compounds from the beans, minimizing the amount of desirable coffee aroma and flavor components which are removed, and minimizing the total time required for treatment of the green or partially roasting beans with the solution.

In terms of duration of treatment, the green or partially roasted beans can be contacted with the treatment solution for a period of from about 1 to about 90 minutes. Longer treatment times maximize the removal of guaiacols and other bitter phenolic compounds. However, these longer treatment times also maximize the removal of desirable coffee aroma and flavor components. Preferably, treatment time is for a period of from about 5 to about 60 minutes. Most preferably, this treatment time is for a period of from about 15 to about 30 minutes.

The treatment of the green or partially roasted beans with the treatment solution can be carried out at temperatures within the range of from about 20° to about 100° C. Lower temperatures minimize the removal and degradation of desirable coffee aroma and flavor components, but slow the removal rate of guaiacols and other bitter phenolic compounds. By contrast, higher temperatures speed up the rate of guaiacol removal, but also increase the removal and degradation of desirable coffee aroma and flavor components. Preferably, this treatment step is carried out at a temperature of from about 25° to about 50° C.

The pressure used during the treatment step is at least about 250 psi. Higher pressures during the treatment step generally favor the removal of guaiacols and other bitter phenolic compounds. The upper level of pressure is generally limited only by the particular equipment used for carrying out the treatment step. Typical pressures used during the treatment step are from about 250 to about 2000 psi. Preferably, the treatment step is carried out under a pressure of from about 500 to about 2000 psi. Basically, any vessel suitable for carrying out high pressure reactions can be used for carrying out the treatment step of the present invention. An example of a suitable high pressure reaction vessel is an autoclave.

In addition to duration, temperature and pressure, another important condition for carrying out the treatment step of the present invention is the particular atmosphere. To avoid or minimize the degradation of desirable aroma components present in the green or partially roasted beans, this treatment step is preferably carried out under an inert, anaerobic (nonoxygen-containing) atmosphere. Suitable atmospheres in this regard are carbon dioxide, nitrogen, argon, and in particular helium.

An optional, but preferred, step is to pretreat the green or partially roasted beans with a guaiacol-depleted coffee liquor or extract (obtained as previously described), followed by treatment with the solution of enzyme according to the process of the present invention. This pretreatment step can be carried out by contacting the partially roasted beans with the guaiacol-depleted liquor or extract for a period of from about 1 to about 60 minutes. Preferably, this pretreatment step is carried for a period of from about 15 to about 30 minutes. This pretreatment step can be carried out under the same temperature, pressure and atmospheric conditions as the treatment step with the solution of enzyme.

C. Roasting and Grinding of Treated Beans

The treated coffee beans can be completely roasted to a final roast color and ground in a conventional manner to provide roast and ground coffee products. Prior to roasting, the treated coffee beans are optionally, but preferably dried. Typically, the treated beans are dried to a moisture content of from about 5 to about 35%. Preferably, the treated beans are dried to a moisture content of from about 7 to about 11%.

Any variety of roasting methods known to the coffee art can be used to completely roast the treated coffee beans. In the normal operation of preparing conventional roast and ground coffee, coffee beans are roasted in a hot gas medium, either in a batch process or a continuous process. The roasting procedure can involve static bed roasting as well as fluidized bed roasting. Typical roasting equipment and methods for roasting coffee beans are disclosed, for example, in Sivetz et al., *Coffee Technology*, Avi Publishing Company, Westport, Conn., 1979, pp. 226–246, which is incorporated by reference. U.S. Pat. No. 3,964,175 to Sivetz, issued June 22, 1976 (herein incorporated by reference), and in particular European patent application No. 132,877 to Price et al, published Feb. 13, 1985 (herein incorporated by reference), disclose suitable methods for fluidized bed roasting of coffee beans.

The treated beans can be roasted to any suitable final roast color. Preferably, the final roast color will be a Hunter L-color of from about 16 to about 24, and most preferably from about 18 to about 22. Darker roasts develop strong flavors that are very desirable in many European countries. Lighter roasts can be used to produce clear, reddish cup colors with slightly weaker flavors.

After final roasting, the coffee beans can be ground according to standard procedures. These standard procedures typically involve cracking, grinding and normalizing. A Gump grinder, manufactured by B. F. Gump Company, Chicago, Illinois, contains both cracking and grinding rolls. Also suitable is a Fitzmill hammer mill, manufactured by Fitzpatrick Manufacturing Co., Elmhurst, Illinois. Some different equipment and methods for cracking, normalizing, and grinding coffee are disclosed in Sivetz et al., *Coffee Technology, supra* at pp. 265–276, which is incorporated by reference. The standard grinds (from coarsest to finest) are electric perk, regular, automatic drip coffee, drip, and fine. Grinding of the coffee can be done in any of the ways known to those skilled on the coffee art. Examples of suitable normalizers are a Gump normalizer or a ribbon blender. The equipment can be modified (especially in length) for optimum industrial use.

If desired, the roast and ground coffee product obtained can be processed further to make soluble or "instant" coffee products. Standard instant coffee processing generally involves three basic steps: (1) countercurrently extracting roast and ground coffee with aqueous extraction liquor; (2) concentrating the resulting extract, preferably to at least a 50% solubles concentration; and (3) freeze-drying or, more typically, spray-drying the concentrated extract to provide a dry instant coffee product. Any of the well-known methods for making instant coffee can be used. Suitable methods and equipment for making instant coffee are disclosed in Sivetz et al., *Coffee Technology, supra* at pp. 317–524, which is incorporated by reference.

Specific Illustrations of Treatment of Partially Roasted Beans According to Process of Present Invention The following are specific illustrations of partially roasted coffee beans treated in accordance with the process of the present invention.

Embodiment 1

A solution of 1300 ml. of water, 130 g. of sucrose, 0.065 g. of rohalase enzyme, and 63.9 microl. of ammonium hydroxide were mixed with 1300 g. of coffee beans which had been partially roasted to a color of 200 photovolts (Hunter L-color of approximately 39). This mixture (weight ratio of solution:beans of about 1:1) was then loaded into the autoclave. After purging with helium, the pressure inside the autoclave was increased to 2000 psi. The contents of the autoclave were held at this pressure for 30 minutes at a temperature of 35° C. The treated beans were then rinsed with distilled water and dried at 250° F. before being completely roasted.

Embodiment 2

Under the same processing conditions described for Embodiment 1, 1000 g. of partially roasted coffee beans were treated with a solution of 1000 ml. of water, 100 g. of sucrose, 0.05 g. of tyrosinase enzyme, and 49.1 microl. of ammonium hydroxide. The weight ratio of solution:beans was about 1:1. The treated beans were then dried before being completely roasted.

Embodiment 3

Green coffee beans are partially roasted to 100 photovolts (Hunter L-color of approximately 26) or 200 photovolts (Hunter L-color of approximately 39), placed in an aqueous solution containing 0.05% rohalase enzyme at a weight ratio of solution:beans of about 2:1 and treated for a period of 15 or 30 minutes at a temperature of 25° or 35° C. and under a pressure of 500, 1000 or 2000 psi, dried to a moisture content of 8 or 10% and then completely roasted and ground to provide a roast and ground coffee product.

Embodiment 4

Green coffee beans are partially roasted to a color of 100 photovolts (Hunter L-color of approximately 26) or 200 photovolts (Hunter L-color of approximately 39), placed in an aqueous solution containing 0.05% rohalase, 5 or 20% sucrose, and 0.005 or 0.01% ammonium hydroxide at a weight ratio of solution:beans of 1:1 and treated for a period of 15 or 30 minutes at a temperature of 25° or 35° C. and under a pressure of 500, 1000 or 2000 psi, dried to a moisture content of 8 or 10%, and then completely roasted and ground to provide a roast and ground coffee product.

Embodiment 5

Green coffee beans are partially roasted to a color of 200 photovolts (Hunter L-color of approximately 39), placed in an essentially guaiacol-free coffee liquor containing rohalase enzyme (weight ratio of solution:beans of 2:1) and treated for a period of 15 or 30 minutes at a temperature of 25° or 35° C. and under a pressure of 500, 1000 or 2000 psi, dried to a moisture content of 8 or 10%, and then completely roasted and ground to provide a roast and ground coffee product.

Roast and ground coffee products can also be obtained according to Embodiments 3, 4 or 5, by substituting tyrosinase, phenolase or coralase L10 enzyme for rohalase enzyme, or by substituting green coffee beans for partially roasted coffee beans.

Embodiment 6

Green coffee beans are partially roasted to a color of 200 photovolts (Hunter L-color of approximately 39), placed in an essentially guaiacol-free coffee liquor (weight ratio of liquor:beans of 2.5:1) and pretreated for a period of 15 or 30 minutes at a temperature of 25° or 35° C. and under a pressure of 500, 1000 or 2000 psi. The coffee liquor is decanted off and the pretreated beans are then placed in an aqueous solution containing 0.05% rohalase enzyme (weight ratio of solution:beans of 1:1). The beans are treated for a period of 15 or 30 minutes at a temperature of 25° or 35° C. and under a pressure of 500, 1000 or 2000 psi, dried to a moisture content of 8 or 10%, and then completely roasted and ground to provide a roast and ground coffee product.

Roast and ground coffee products can also be obtained according to Embodiment 6 by substituting tyrosinase, phenolase or coralase L10 enzyme for rohalase enzyme, or by substituting green coffee beans for partially roasted coffee beans.

What is claimed is:

1. A process for reducing the bitterness and enhancing the aroma and flavor of roast and ground coffee, said process comprising the steps of:
   (a) partially roasting green coffee beans to a Hunter L-color of from about 26 to about 44;
   (b) drying the partially roasted beans to a moisture content of from about 1.5 to about 4%;
   (c) treating the dried, partially roasted beans under an inert, anaerobic atmosphere with an aqueous solution containing from about 0.005 to about 0.5% by weight of the beans of an enzyme selected from the group consisting of hemicellulases, cellulases, proteases, phenol oxidases and mixtures thereof, from about 5 to about 20% by weight of a sugar and from about 0.01 to about 0.02% by weight of a foodgrade base, for a period of from about 5 to about 60 minutes at a temperature of from about 20° to about 100° C. and under a pressure of from about 250 to about 2000 psi, the weight ratio of solution to beans being from about 1:6 to about 3:1;

(d) drying the treated beans to a moisture content of from about 7 to about 11%;

(e) completely roasting the dried, treated beans to a final Hunter L-color of from about 16 to about 24; and (f) grinding the completely roasted beans to provide roast and ground coffee.

2. The process of claim 1 wherein the dried, partially roasted beans are treated with the aqueous solution for a period of from about 15 to about 30 minutes at a temperature of from about 25° to about 50° C. during step (c).

3. The process of claim 2 wherein the pressure during step (c) is from about 500 to about 2000 psi.

4. The process of claim 2 wherein the aqueous solution comprises coffee liquor or coffee extract.

5. The process of claim 4 wherein the aqueous solution comprises coffee liquor obtained from partially roasted coffee beans.

6. The process of claim 4 wherein the coffee liquor or coffee extract is at least partially depleted of guaiacols.

7. The process of claim 4 wherein the sugar is selected from the group consisting of sucrose, fructose, glucose and mixtures thereof.

8. The process of claim 7 wherein the foodgrade base is ammonium hydroxide.

9. The process of claim 8 wherein the weight ratio of solution to beans is from about 1:2 to about 2:1.

10. The process of claim 9 wherein the enzyme is selected from the group consisting of rohalase, coralase L10, tyrosinase, phenolase and mixtures thereof.

11. The process of claim 10 wherein the dried, partially roasted beans are pretreated under an inert, anaerobic atmosphere with a guaiacol-depleted coffee liquor or coffee extract prior to step (c) for a period of from about 15 to about 30 minutes at a temperature of from about 25° to about 50° C. and under a pressure of from about 250 to about 2000 psi.

* * * * *